United States Patent
Carter (10) Patent No.: US 6,663,614 B1
(45) Date of Patent: Dec. 16, 2003

(54) CATHETER SHAFT HAVING VARIABLE THICKNESS LAYERS AND METHOD OF MAKING

(75) Inventor: Mark Carter, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 79 days.

(21) Appl. No.: 09/707,681

(22) Filed: Nov. 6, 2000

(51) Int. Cl.$^7$ .............................................. A61M 25/00
(52) U.S. Cl. ...................... 604/525; 604/264
(58) Field of Search .................. 604/523, 524, 604/525, 264, 915; 600/139, 140, 433–435, 523, 525, 534

(56) References Cited

U.S. PATENT DOCUMENTS

| | | | |
|---|---|---|---|
| 3,752,617 A | 8/1973 | Burlis et al. ................ | 425/131 |
| 4,250,072 A | 2/1981 | Flynn .................... | 260/31.2 N |
| 4,276,250 A | 6/1981 | Satchell et al. ............. | 264/167 |
| 4,330,497 A | 5/1982 | Agdanowski ............... | 264/150 |
| 4,385,635 A | 5/1983 | Ruiz ......................... | 128/658 |
| 4,495,134 A | 1/1985 | Ouchi et al. ................ | 264/516 |
| 4,551,292 A | 11/1985 | Fletcher et al. ............. | 264/139 |
| 4,636,346 A | 1/1987 | Gold et al. ................. | 264/139 |
| 4,739,768 A | 4/1988 | Engelson | |
| 4,775,371 A | 10/1988 | Mueller, Jr. ................ | 604/280 |
| 4,824,618 A | 4/1989 | Strum et al. ................ | 264/37 |
| 4,842,590 A | 6/1989 | Tanabe et al. .............. | 604/282 |
| 4,846,814 A | 7/1989 | Ruiz ......................... | 604/281 |
| 4,886,506 A | 12/1989 | Lovgren et al. ............ | 604/280 |
| 4,888,146 A | 12/1989 | Dandeneau ................ | 264/171 |
| 4,904,431 A | 2/1990 | O'Maleki ................... | 264/103 |
| 4,976,690 A | 12/1990 | Solar et al. ................ | 604/96 |
| 4,983,169 A | 1/1991 | Furukawa ................... | 604/164 |
| 5,035,596 A | 7/1991 | Pohl ......................... | 425/133.1 |
| 5,059,375 A | 10/1991 | Lindsay ..................... | 264/167 |
| 5,085,649 A | 2/1992 | Flynn ........................ | 604/282 |
| 5,125,913 A | 6/1992 | Quackenbush .............. | 604/264 |
| 5,258,160 A | 11/1993 | Utsumi et al. .............. | 264/558 |
| 5,308,342 A | 5/1994 | Sepetka et al. | |
| 4,739,768 A | 11/1994 | Engelson | |
| 5,437,632 A | 8/1995 | Engelson | |
| 4,739,768 A | 10/1995 | Engelson | |
| 5,456,674 A | 10/1995 | Bos et al. .................... | 604/280 |
| 5,499,973 A | 3/1996 | Saab | |
| 5,533,985 A | 7/1996 | Wang ......................... | 604/264 |
| 5,542,937 A | 8/1996 | Chee et al. ................. | 604/280 |
| 5,599,326 A | 2/1997 | Carter ........................ | 604/282 |
| 5,614,136 A | 3/1997 | Pepin et al. ................ | 264/40.3 |
| 5,622,665 A | 4/1997 | Wang ......................... | 264/150 |
| 5,725,814 A | 3/1998 | Harris ........................ | 264/40.3 |
| 5,749,849 A | 5/1998 | Engelson ..................... | 604/53 |
| 5,895,378 A | 4/1999 | Berenstein et al. | |
| 6,030,369 A | 2/2000 | Engelson et al. ........... | 604/264 |
| 6,045,547 A | 4/2000 | Ren et al. ................... | 604/525 |
| 6,217,565 B1 | 4/2001 | Cohen | |
| 6,217,566 B1 | 4/2001 | Ju et al. | |
| 6,524,299 B1 | 2/2003 | Tran et al. | |

FOREIGN PATENT DOCUMENTS

| | | |
|---|---|---|
| DE | 40 32 869 A1 | 10/1990 |
| EP | 0729766 | 9/1996 |
| WO | WO 95/29051 | 11/1995 |

*Primary Examiner*—Manuel Mendez
(74) *Attorney, Agent, or Firm*—Fulwider Patton Lee & Utecht, LLP (57) ABSTRACT

A catheter having a shaft with at least two variable layers, in which the relative proportions of the two layers changes along at least a part of the multilayered shaft section. The catheter shaft includes a cotapered transition section having a first layer tapering to a decreased thickness, and a second layer inversely tapering to an increased thickness. In one embodiment, the shaft has one or more tapered outer and/or inner surfaces in addition to the cotapered transition. The tapered, outer or inner surface of the shaft is typically longitudinally displaced from the cotapered transition section. In a presently preferred embodiment, the shaft having a cotapered transition section is coextruded. Another aspect of the invention includes a method of making a shaft having a cotapered transition section. The shaft of the invention provides improved transitions between shaft sections, to thereby change characteristics such as the shaft stiffness along the length of the catheter.

15 Claims, 5 Drawing Sheets

CATHETER SHAFT HAVING VARIABLE THICKNESS LAYERS AND METHOD OF MAKING

BACKGROUND OF THE INVENTION

This invention generally relates to catheters, and particularly intravascular catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy where the balloon of the dilatation catheter is positioned within the stenosis to be dilated. The balloon is then inflated with radiopaque liquid at relatively high pressures (generally 4–16 atmospheres) to dilate the stenosed region of the diseased artery. One or more inflations may be needed to effectively dilate the stenosis.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

An essential step in effectively performing a PTCA procedure is properly positioning the balloon catheter at a desired location within the coronary artery. To properly position the balloon at the stenosed region, the catheter must have good pushability and flexibility, to be readily advanceable within the tortuous anatomy of the patient's vasculature. Conventional catheter shafts may typically include multiple shaft sections having different flexibilities along the length of the catheter to improve the maneuverability of the catheter. A variety of methods have been used to form shafts having sections with variable flexibility, including forming multilayered shafts having transition sections in which a first layer tapers to a larger thickness as a second layer tapers inversely to a smaller thickness. One difficulty has been controlling the changes in the thickness of the first layer and second layer. Insufficient control, resulting in disadvantageously abrupt or gradual changes in the proportions of a first and second polymer, may result from conventional coextrusion systems, such as those using on/off valves to control the flow of the polymers making up the two layers. U.S. Pat. No. 5,725,814 (Harris), incorporated by reference herein in its entirety, discloses a coextrusion apparatus having gear pumps at the output ends of multiple extruders. The gear pumps are used to vary the relative amount of the polymers extruded and to thus form an extruded tube having multiple layers, the proportions of which vary along the length of the extruded tube.

What has been needed is a catheter which is highly trackable within the patient's anatomy, with improved flexibility and pushability.

SUMMARY OF THE INVENTION

This invention is directed to a catheter having a shaft with at least two variable layers, wherein the relative proportions of the two layers change along at least a section of the multilayered shaft. The catheter shaft includes a section having a first layer tapering to a decreased thickness, and a second layer inversely tapering to an increased thickness, referred to herein as a cotapered transition section. The term inversely tapering should be understood to mean the second layer tapers in an opposite direction to the taper of the first layer. In one embodiment, the shaft has one or more tapered outer and/or inner surfaces in addition to the cotapered transition. The tapered outer or inner surface section of the shaft is typically longitudinally displaced from the cotapered transition section and may be directly adjacent to the cotapered transition section. In a presently preferred embodiment, the shaft having a cotapered transition section is coextruded. Another aspect of the invention includes a method of making a shaft having a cotapered transition section. The shaft of the invention provides improved transitions between shaft sections, to thereby change characteristics such as the shaft stiffness along the length of the catheter.

In one embodiment of the invention, the catheter shaft has a first longitudinal section having a cotapered transition section with a first layer having a tapered surface and a second layer having an inversely tapered surface, and a second longitudinal section with a tapered outer diameter. One of the first or the second layers has a tapered inner surface and a tapered outer surface in the second longitudinal section of the catheter shaft, and one of the first or second layers has a substantially constant wall thickness in the second longitudinal section of the catheter shaft. The first longitudinal section may be proximal or distal to the second longitudinal section, and the first layer may be an inner layer or an outer layer relative to the second layer.

In another embodiment of the invention, the catheter shaft has a first longitudinal section having a cotapered transition section with a first layer having a tapered surface and a second layer having an inversely tapered surface, and a second longitudinal section with a tapered outer diameter and with the first layer having a substantially constant wall thickness from at least a portion of the second longitudinal section to the distal end of the catheter shaft. In a presently preferred embodiment, the first longitudinal section is proximal to the second longitudinal section, and the first layer is an inner layer relative to the second layer.

In another embodiment, the catheter shaft has a first longitudinal section having a cotapered transition section with a first layer having a tapered surface and a second layer having an inversely tapered surface, and a second longitudinal section distal to and directly adjacent to the first longitudinal section, with a tapered outer diameter and with the first layer having an outer surface tapering distally to a smaller outer diameter and the second layer having an outer surface tapering distally to a smaller outer diameter. The first longitudinal section may be proximal or distal to the second longitudinal section, and the first layer may be an inner layer or an outer layer relative to the second layer. The first and second layers may be extend along the entire length of the shaft, or may have a proximal end and/or a distal end which terminate between the proximal and distal ends of the shaft.

In one embodiment, the catheter is a balloon catheter generally including an elongated shaft having a cotapered transition section in accordance with the invention and a balloon secured to a distal portion of the shaft.

A method of making an elongated multilayered catheter shaft having at least a first layer and a second layer and having a cotapered section in which the first layer tapers from a larger wall thickness to a smaller wall thickness and the second layer inversely tapers from a smaller wall thickness to a larger wall thickness, includes extruding the first layer from an extruder having a first pump at an output end thereof, and extruding the second layer from a second extruder having a second pump at an output end thereof. The first and second pumps are preferably gear pumps. The first and second layers are preferably coextruded through a coextrusion die downstream from the first and second extruders and first and second gear pumps. The direction of the first pump, e.g., the rotation of the first gear pump, is reversed to at least in part form the tapered surface in the first layer, and the speed of the second pump is increased from a first speed to a second speed to form the inverse taper in the second layer. As a result of temporarily setting the first gear pump into reverse rotation, plastic pressure is removed from the layer being tapered, and the time required to taper the first layer from the larger to the smaller wall thickness is advantageously reduced, to thereby produce a tailored, shorter transition. In one embodiment, forming the cotapered section includes temporarily speeding up the speed of the second gear pump from a first speed to a second speed which is greater than the steady state third speed used to form a section of the shaft after the cotapered section, to thereby reduce the time required to taper the second layer from the smaller wall thickness to the larger wall thickness. Thus, in one embodiment, a section of the shaft, which is adjacent and distal to the cotapered section, is formed by decreasing the speed of the second gear pump from the second speed used to form the cotapered section to a third speed greater than the first speed used to form a section of the shaft before the cotapered section and less than the second speed. The method of the invention provides improved short transitions varying the relative proportions of the first and second layers. The tailored short transitions are particularly advantageous in distal sections of the catheter shaft, to provide rapid changes in flexural modulus of the shaft for improved maneuverability of the catheter in the highly tortuous distal vascular anatomy.

Preferably, the polymer forming the first layer is different from the polymer forming the second layer. The polymer forming the inner layer of the cotapered section may have a hardness greater than, less than or equal to the hardness of the outer layer. In one embodiment, the viscosity of the polymers used to form the first and second layers is selected to minimize back pressure between the gear pumps and the die, and more specifically to minimize stored pressure energy which leads to long transitions.

The catheter shaft of the invention has excellent flexibility, pushability, and trackability due to the variable layers of the shaft having improved tapered transitions. The tapered transitions provide improved force transmission, cross, and flexibility in the distal end of the catheter, and tailoring of the catheter shaft characteristics, while avoiding the increased profile and increased risk of kinking in conventional fusion or adhesion junctions used to secure separate shaft sections together. The catheter shaft of the invention avoids significant negative effects on inflation/deflation time caused by disadvantageous decreases in the size of the shaft lumen(s) at bonded junctions. Additionally, one embodiment of the invention involves providing a catheter shaft having a tailored, short transition, providing improved rapid changes in the shaft flexural modulus while avoiding disadvantageously abrupt transitions. These and other advantages of the invention will become more apparent from the following detailed description when taken in conjunction with the accompanying exemplary drawings.

DETAILED DESCRIPTION OF THE INVENTION

Figure 1:
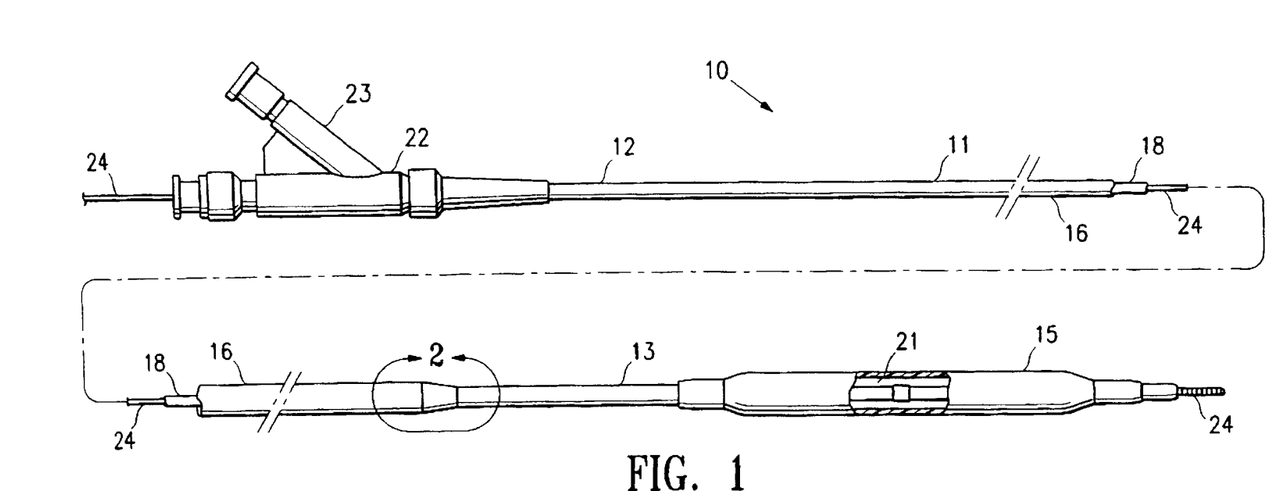
FIG. 1 is an elevational view, partially in section, of a balloon catheter which embodies features of the invention.
Figure 2:
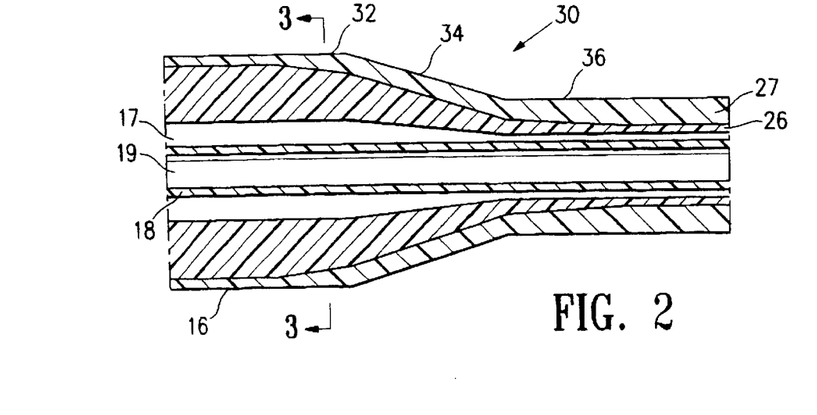
FIG. 2 is an enlarged longitudinal cross sectional view of the catheter shown in FIG. 1, taken within circle 2, illustrating a shaft section having a proximal longitudinal section with cotapered inner and outer layers, and a distal longitudinal section with a tapered outer diameter and the inner layer having a tapered inner surface and a tapered outer surface and the outer layer having a substantially constant wall thickness in the distal longitudinal section.

FIG. 1 illustrates an intraluminal catheter 10 which embodies features of the invention, generally comprising an elongated shaft 11 having a proximal end 12 and a distal end 13. Catheter 10 is a balloon catheter having a balloon 15 secured to a distal portion of the shaft 11. In the embodiment illustrated in FIG. 1, the shaft 11 comprises an outer tubular member 16 defining in part an inflation lumen 17 (FIG. 2), and an inner tubular member 18 disposed within the outer tubular member and defining a guidewire lumen 19 (FIG. 2) configured to slidably receive a guidewire 24. In the illustrated embodiment, the coaxial relationship between outer tubular member 16 and inner tubular member 18 defines annular inflation lumen 17. Balloon 15 has a proximal end sealingly secured to the distal end of outer tubular member 16 and a distal end sealingly secured to the distal end of inner tubular member 18, so that its inflatable interior 21 is in fluid communication with inflation lumen 17. Adapter 22 at the proximal end of the shaft 11 is configured to direct inflation fluid through arm 23 into inflation lumen 17, and provide access to guidewire lumen 19. In accordance with the invention, at least a section of the catheter shaft 11 has section hereinafter referred to as a cotapered section with a first layer 26 having a tapered surface and a second layer 27 having an inversely tapered surface. FIG. 2, illustrates an enlarged longitudinal cross section of a distal portion of the catheter 10 shown in FIG. 1, taken along lines 2—2.

FIGS. 4–7 illustrate alternative embodiments of a catheter shaft which embodies features of the invention.

Figure 3:
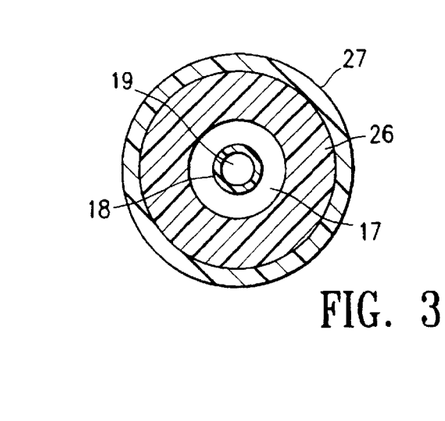
FIG. 3 is a transverse cross-section of the catheter shaft section shown in FIG. 2, taken along line 3—3.

In the embodiment illustrated in FIG. 2, the shaft 11 has a first layer 26 which is an inner layer, and a second layer 27 which is an outer layer. The shaft section 30 of the shaft 11 illustrated in FIG. 2 has a first longitudinal section 32, a second longitudinal section 34, and a third longitudinal section 36. In the embodiment illustrated in FIG. 2, the shaft section 30 is a section of the outer tubular member 16. However, the shaft section 30 may be used in a variety of shaft designs including a section of inner tubular member 18, or a section of an extruded single, dual or multilumen lumen shaft. FIG. 3 illustrates a transverse cross sectional view of the shaft 11 shown in FIG. 2, taken along line 2—2. In the shaft first longitudinal section 32 the inner and outer layers 26/27 cotaper, so that the inner layer has a tapered surface and the outer layer 27 has a surface tapering inversely thereto. The first longitudinal section 32 is proximal to second longitudinal section. The second longitudinal section 34 has a tapered outer diameter. Thus, in the embodiment illustrated in FIG. 2, the distal end of the first longitudinal section 32 is at the location on the shaft where the outer diameter of the shaft begins to taper. In the second longitudinal section 34, the inner layer 26 has a tapered inner surface and a tapered outer surface, and the outer layer 27 has a substantially constant wall thickness. In the embodiment illustrated in FIG. 2, the shaft 11 includes third longitudinal section 36 distal to the second longitudinal section 34 with the inner layer 26 and outer layer 27 cotapering. The third longitudinal section 36 has a substantially constant outer diameter less than the outer diameter of the first longitudinal section 32.

Figure 4:
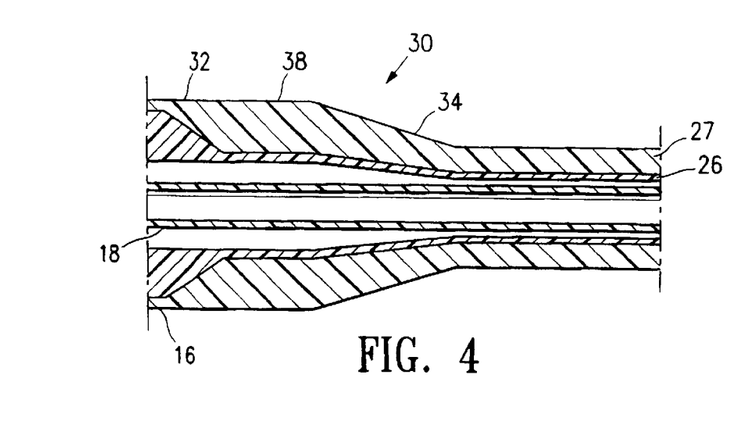
FIG. 4 is an enlarged longitudinal cross sectional view of another embodiment of a catheter shaft which embodies features of the invention, illustrating a shaft section having a proximal longitudinal section with cotapered inner and outer layers, and a distal longitudinal section with a tapered outer diameter and the inner layer having a substantially constant wall thickness in the distal longitudinal section and the outer layer having a tapered inner surface and a tapered outer surface in the distal longitudinal section.

In the embodiment illustrated, in FIG. 4, the first longitudinal section 32 of the catheter shaft, having cotapered first and second layers 26/27, is proximal to the second longitudinal section 34 having a tapered outer diameter. The first layer 26 is an inner layer, and the second layer 27 is an outer layer. In the second longitudinal section 34, the outer layer 27 has a tapered inner surface and a tapered outer surface, and the inner layer 26 has a substantially constant wall thickness. In the embodiment illustrated in FIG. 4, the shaft 11 includes an intermediate shaft section 38 between and directly adjacent to the first and second longitudinal sections 32/34 of the catheter shaft, having a constant outer diameter. In the embodiment illustrated in FIG. 4, the inner surface of the outer layer 27 and the outer surface of the inner layer 26 are not tapered in the intermediate section 38, so that the intermediate section 38 has a constant interfacial diameter between the inner and outer layers 26/27. It should be understood that, as discussed above in relation to the embodiment shown in FIG. 2, the shaft section 30 illustrated in FIG. 4 and in the remaining figures may be used in a variety of shaft designs, as a section of an inner and/or outer tubular member, or a section of an extruded single, dual or multilumen lumen shaft.

Figure 5:
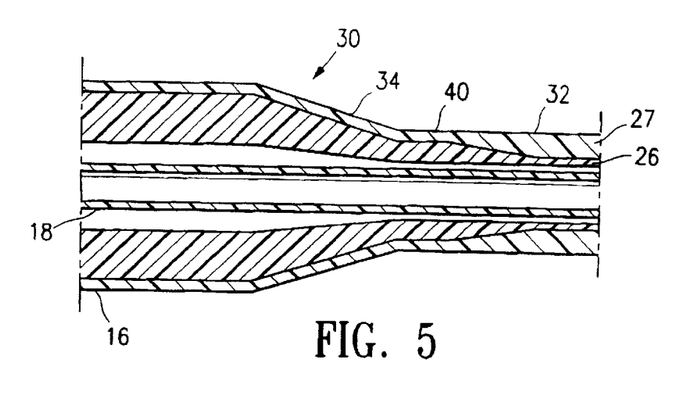
FIG. 5 is an enlarged longitudinal cross sectional view of another embodiment of a catheter shaft which embodies features of the invention, illustrating a shaft section having a proximal longitudinal section with a tapered outer diameter and with an inner layer having a tapered inner surface and a tapered outer surface and the outer layer having a substantially constant wall thickness in the proximal longitudinal section, and a distal longitudinal shaft section with cotapered inner and outer layers.

In the embodiment illustrated in FIG. 5, the first longitudinal section 32, having cotapered first and second layers 26/27, is distal to the second longitudinal section 34, having a tapered outer diameter. The first layer 26 is an inner layer, and the second layer 27 is an outer layer. In the second longitudinal section 34, the inner layer 26 has a tapered inner surface and a tapered outer surface, and the outer layer 27 has a substantially constant wall thickness. In the embodiment illustrated in FIG. 5, the shaft 11 includes an intermediate section 40 between the first longitudinal section 32 and the second longitudinal section 34, with inner and outer layers 26/27 having a constant interfacial diameter in the intermediate section 40.

Thus, in the embodiments illustrated in FIGS. 2, 4 and 5, the catheter shaft 11 comprises a shaft section 30 having a first longitudinal section 32 with a first layer 26 having a tapered surface, and a second layer 27 having an inversely tapered surface, and a second longitudinal section 34 with a tapered outer diameter, one of the first or the second layers 26/27 having a tapered inner surface and a tapered outer surface in the second longitudinal section 34, and one of the first or the second layers 26/27 having a substantially constant wall thickness in the second longitudinal section 34.

Figure 6:
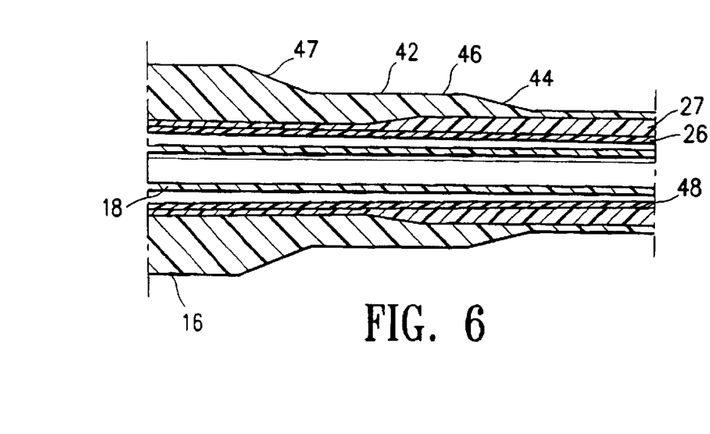
FIG. 6 is an enlarged longitudinal cross sectional view of another embodiment of a catheter shaft which embodies features of the invention, illustrating a shaft section having a proximal longitudinal shaft section with cotapered inner and outer layers, and a distal longitudinal shaft section with a tapered outer diameter, the first layer having a substantially constant wall thickness from a location on the distal longitudinal section to the distal end of the multilayered shaft.

In an alternative embodiment of the invention illustrated in FIG. 6, the shaft comprises a first longitudinal section 42 with cotapered first and second layers 26/27, and a second longitudinal section 44 with a tapered outer diameter. In the embodiment illustrated in FIG. 6, the first longitudinal section 42 is proximal to the second longitudinal section 44. The first layer 26 is an inner layer, and the second layer 27 is an outer layer. In the second longitudinal section 44, the first layer 26 has a substantially constant wall thickness from at least a portion of the second longitudinal section preferably to an end of the multilayered shaft 11. In the embodiment illustrated in FIG. 6, the first longitudinal section 42 has a substantially constant outer diameter. In the embodiment illustrated in FIG. 6, an intermediate section 46 having a constant outer diameter and a constant interfacial diameter between the inner and outer layers 26/27 is provided between first longitudinal section 42 and second longitudinal section 44, and a proximal tapered section 47 having a tapered outer diameter is provided proximal to the cotapered first longitudinal section 42.

In the embodiment illustrated in FIG. 6, an inner liner 48 on an inner surface of the first layer 26 defines the inner lumen of the shaft 11 outer tubular member 16. Preferably, the inner liner 48 is a lubricious material, such as HDPE or a fluoropolymer such as teflon. Although illustrated as an inner liner on an outer tubular member, the inner liner 48 may be provided on a shaft section defining a lumen configured for slidably receiving members such as guidewires, mandrels, and diagnostic or therapeutic instruments therein, to facilitate advancement of such members therein. In the illustrated embodiment, the liner 48 has a substantially constant wall thickness.

Figure 7:
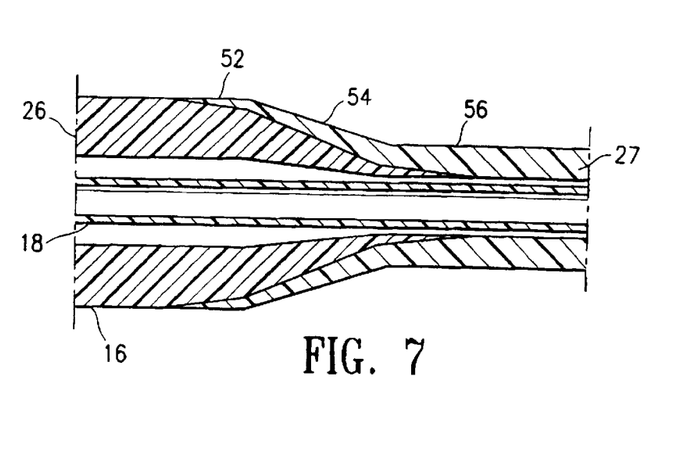
FIG. 7 is an enlarged longitudinal cross sectional view of another embodiment of a catheter shaft which embodies features of the invention, illustrating a shaft section having cotapered inner and outer layers, the inner layer having a distal end proximal to the distal end of the outer layer, and the outer layer having a proximal end distal to the proximal end of the inner layer.

In an alternative embodiment illustrated in FIG. 7, the shaft comprises a first longitudinal section 52 with cotapered first layer 26 and second layer 27, and a second longitudinal section 54 with a tapered outer diameter. In the embodiment illustrated in FIG. 7, the first longitudinal section 52 is proximal to the second longitudinal section 54, and the first layer 26 is an inner layer and the second layer 27 is an outer layer. In the second longitudinal section 54, the inner layer 26 and the outer layer 27 each have an outer surface tapering distally to a smaller outer diameter. The shaft includes a third longitudinal section 56 distal to the second longitudinal section 54, with the inner layer 26 and outer layer 27 cotapering in the third longitudinal section 56. The third longitudinal section 56 has a substantially constant outer diameter less than the outer diameter of the first longitudinal section 52. In the embodiment illustrated in FIG. 7, the first and second layers 26/27 do not extend the length of the shaft 11, so that the distal end of the first layer 26 is proximal to the distal end of the second layer 27, and the proximal end of the second layer 27 is distal to the proximal end of the first layer 26. Specifically, in the embodiment illustrated in FIG. 7, the distal end of the first layer 26 terminates at the distal end of the cotapered third longitudinal section 56, and the proximal end of the second layer 27 terminates at the proximal end of the cotapered first longitudinal section 52. In alternative embodiments, the first and second layers are continuous, extending from the proximal to the distal end of the shaft 11.

The inner layer may be provided with an inner surface tapering distally to a smaller inner diameter, such as the inner layer 26 illustrated in FIGS. 2, 4, 5 and 7 having the inner layer tapering distally in the second longitudinal section 34/54 of the shaft. Alternatively the inner layer 26 may have a substantially constant inner diameter. The terminology substantially constant should be understood to mean that the diameter of the shaft or wall thickness of the individual layer of the shaft is not intentionally tapered and is therefore constant within the tolerances of the method used to form the member. Thus, for an extruded shaft section, the substantially constant outer diameter of an individual layer preferably varies by not more than about ±0.001 inch, and the substantially constant wall thickness of an individual layer preferably varies by not more than about ±0.0005 inch.

The first layer 26 and the second layer 27 may be formed of a variety of suitable polymeric materials depending on the configuration of the shaft and the desired use and characteristics of the shaft. In a presently preferred embodiment, the first and second layers 26/27 are formed of polymeric materials having different characteristics such as Shore Durometer hardness, softness, and lubricity. In one embodiment, the polymeric material which is present in a larger relative proportion in the distal shaft section than in the proximal shaft section, such as the outer layer in the embodiment of FIG. 2, is formed of a polymeric material having a lower Shore Durometer hardness than the polymeric material forming the other layer, to thus provide a relatively flexible distal shaft section. Presently preferred polymeric materials used to form the outer layer in the embodiment of FIG. 2 include polyamides such as nylon, polyamide block copolymers such as Pebax (polyether block amide), polyethylene based adhesives such as PRIMACOR, polyolefins, low density polyethylene (LDPE), high density polyethylene (HDPE), polyurethane, and polyesters such as HYTREL or ARNITEL. Presently preferred polymeric materials used to form the outer layer in the embodiment of FIG. 2 have a Shore durometer hardness of about 90A to about 70D, preferably about 50D to about 60D. However, the choice of material depends on a variety of factors including the desired application and the method used to make the shaft. In one presently preferred embodiment, the inner layer is a lubricious material, to facilitate advancement of members such as guidewires therein. However, a thin lubricious liner on an inner surface of the inner layer may be used to provide the desired lubricity to the wall defining the inner lumen of the shaft. Presently preferred polymeric materials used to form the inner layer in the embodiment of FIG. 2 include polyamide block copolymers such as Pebax, polyurethanes, polyesters such as HYTREL or ARNITEL, and polyolefins such as HDPE. Presently preferred polymeric materials used to form the inner layer in the embodiment of FIG. 2 have a Shore durometer hardness of about 60D to about 82D. In one embodiment, the polymeric materials used to form the inner and outer layers are compatible, and can be heat bonded together.

Figure 8:
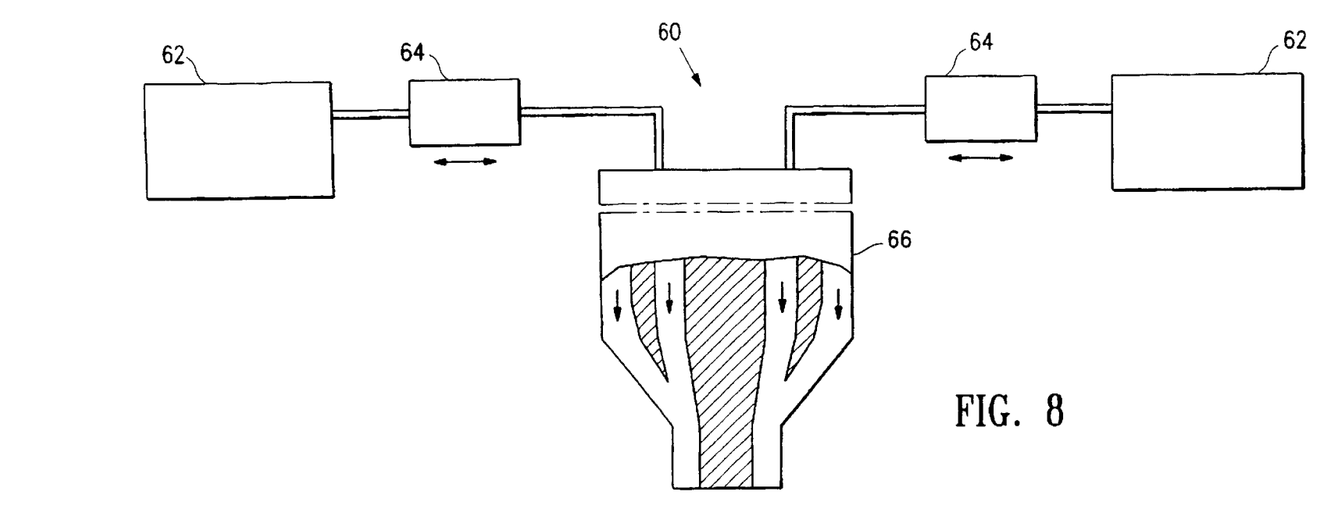
FIG. 8 is a schematic block diagram of a co-extrusion apparatus useful in extruding polymeric tubes according to a method which embodies features of the invention.
Figure 11:
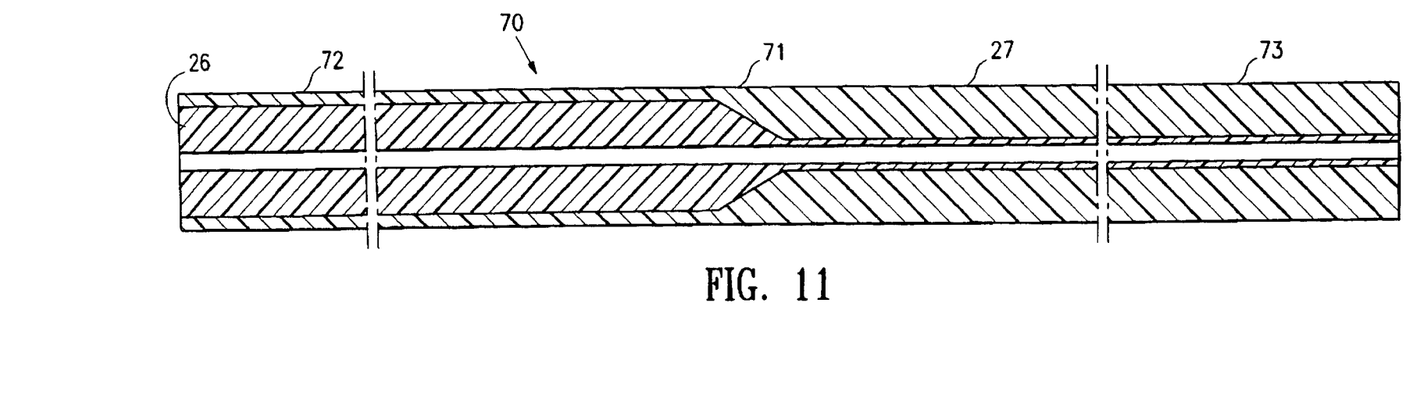
FIG. 11 is an enlarged longitudinal cross sectional view of another embodiment of a catheter shaft which embodies features of the invention, having cotapered inner and outer layers formed according to a method which embodies features of the invention.

FIG. 8 illustrates an apparatus 60 useful in a method of making a cotapered section which embodies features of the invention. Apparatus 60 generally comprises at least two extruders 62, each extruder having a pump 64, which in a presently preferred embodiment is a gear pump, at an output end of the extruder 62. A coextrusion cross-head 66 with a coextrusion cross-head die is at the output end of each gear pump 64. Additional extruders 62 and corresponding gear pumps 64 can be provided if a catheter shaft having more than two coextruded cotapered layers are desired. A control system (not shown) is provided to control the extruders and pumps. The gear pumps are used to vary the relative amount of the polymers extruded to form a cotapered section. In one embodiment of the invention, a gear pump 64 is temporarily set into reverse rotation to form the cotapered layer tapering from a larger wall thickness to a smaller wall thickness. In another embodiment, a gear pump 64 is temporarily sped up beyond the steady state operating speed of the gear pump to form the cotapered layer tapering from a smaller wall thickness to a larger wall thickness. A method of making an elongated multilayered catheter shaft, generally comprises extruding a first layer from an extruder having a first gear pump at an output end thereof, and coextruding a second layer with the first layer from a second extruder having a second gear pump at an output end thereof. FIG. 11 illustrates an elongated shaft 70 formed according to a method of the invention, having a first layer 26, a second layer 27, a cotapered section 71, a proximal section 72 and a distal section 73. Cotapered section 71 of the shaft is formed by reversing the rotation of the first gear pump 64 to at least in part form the taper in the first layer 26 tapering from a greater wall thickness to a smaller wall thickness. Thus, the speed of the first gear pump 64 in the forward direction is reduced to zero and then the speed in the reverse direction is increased to a value greater than zero. The speed setting of the first gear pump 64 in the reverse direction may be less than, equal to, or greater than the speed setting of the first gear pump in the forward direction. The outer or inner tapered surfaces of the shaft, such as the tapered outer surface of the outer layer 27 in the second longitudinal section 34 in the embodiment of FIG. 2 can be formed using conventional tapering methodology such as increasing the speed of the puller (not shown) which draws or elongates the extrudate exiting the die 66.

Conventional details regarding the configuration of the co-extrusion apparatus 60 used in the method of the invention, including the functioning of the extruders and the relative operation of the apparatus components can be found in U.S. Pat. No. 5,725,814, previously incorporated by reference.

The thickness of the first layer 26 and the second layer 27 in the proximal shaft section 72 and the distal shaft section 73 will depend on the materials used to form the shaft and the desired use and characteristics of the shaft. In one embodiment, the hardness of the polymer forming first layer 26 (the inner layer in FIG. 11) is greater than the hardness of the polymer forming the second layer 27 (the outer layer in FIG. 11), which in the embodiment illustrated in FIG. 11 provides a relatively more flexible distal shaft section and a relatively less flexible proximal shaft section. However, in alternative embodiments the first layer 26 may be formed of a polymeric material having a hardness less than the hardness of the second layer polymeric material. Additionally, reinforcements, such as braided or wound metal or polymer members may be provided in one or more sections of one or more of the layers.

Figure 9:
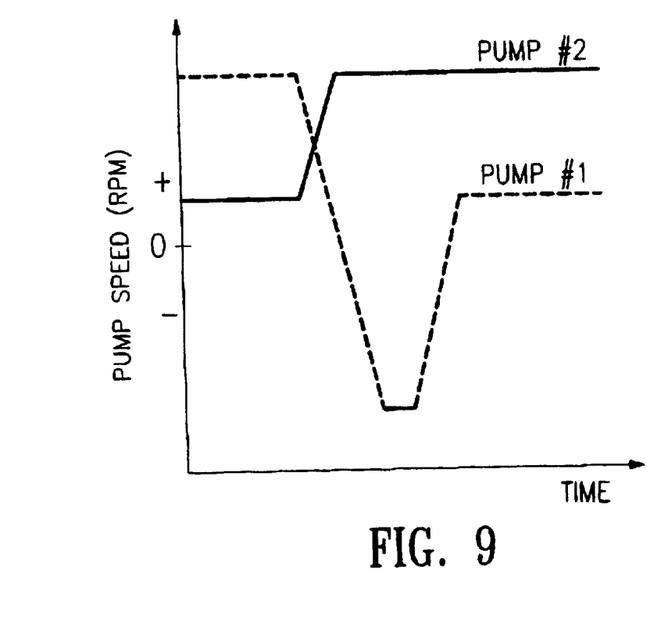
FIG. 9 is a graph of gear pump speed versus time useful in extruding polymeric tubes according to a method which embodies features of the invention, in which the first gear pump extruding the first layer being tapered from thick to thin is temporarily reversed.

FIG. 9 is a graph of the gear pump 64 speed versus time, useful in a method which embodies features of the invention in which the first gear pump 64 is temporarily reversed to extrude the first layer 26 being tapered from thick to thin in the cotapered section. For illustration purposes, the method will be discussed in terms of the embodiment of the catheter shaft illustrated in FIG. 11 where catheter shaft 70 has at least first layer 26 (hereafter the inner layer) and second layer 27 (hereafter the outer layer) and a co-tapered section 71 in which the inner layer tapers distally to a smaller wall thickness and the outer layer tapers inversely to the taper of the first layer, although the method can be used to form a variety of shaft designs embodying features of the invention. The inner layer comprises a first polymer formed of, for example, nylon, HDPE, or HYTREL, having a Shore durometer hardness of about 60D to about 82D, and the outer layer comprises a second polymer formed of, for example, Pebax, LDPE, or HYTREL, having a Shore durometer hardness of about 55D to about 63D. In one embodiment, the inner and outer layers are compatible materials, so that the outer layer is Pebax when the inner layer is nylon, or LDPE when the inner layer is HDPE, or HYTREL when the inner layer is HYTREL. The proximal shaft section 72 is made by extruding first polymer from the first extruder 62 at a temperature between about 300° F. to about 600° F. with the first gear pump in the forward direction at a speed of about 2 rpm to about 60 rpm, preferably about 5 rpm to about 7 rpm, for about 0.5 seconds to about 20 seconds, preferably about 1 second to about 3 seconds, and at the same time coextruding second polymer from the second extruder 62 at a temperature between about 300° F. to about 600° F. with the second gear pump in the forward direction at a speed of about 0.25 rpm to about 10 rpm, preferably about 0.25 rpm to about 0.75 rpm, for about 0.5 seconds to about 20 seconds, preferably about 1 second to about 3 seconds, to form inner and outer layers 26/27, respectively, in the proximal section 72 of the shaft. The gear pump may be set to a speed of about 0 rpm to taper the layer to a zero thickness, or to merely decrease the thickness of the layer without tapering to a zero thickness when the extruded material does not quickly reflect the zero rpm pump setting. To form the cotapered section 71 of the shaft, the rotation of the first gear pump 64 is reversed, so that the first gear pump ramps down to a negative speed setting of about −1 rpm to about −10 rpm in about 0.1 seconds to about 2 seconds (i.e., ramps down at a rate of about 100 rpm/seconds) to form the taper in the inner layer 26 of the cotapered section 71, and the second gear pump ramps up to a speed of about 2 rpm to about 60 rpm, preferably about 2 rpm to about 20 rpm, in about 0.1 seconds to about 2 seconds, preferably about 0.1 seconds to about 0.2 seconds to form the taper in the outer layer 26 of the cotapered section 71. The first gear pump is typically held at the negative speed setting for about 0.25 seconds to about 1 second, before being set in a forward rotation of about 0 rpm to about 10 rpm, preferably about 0.25 to about 0.75 rpm, to form the inner layer 26 of the distal shaft section 73.

Figure 10:
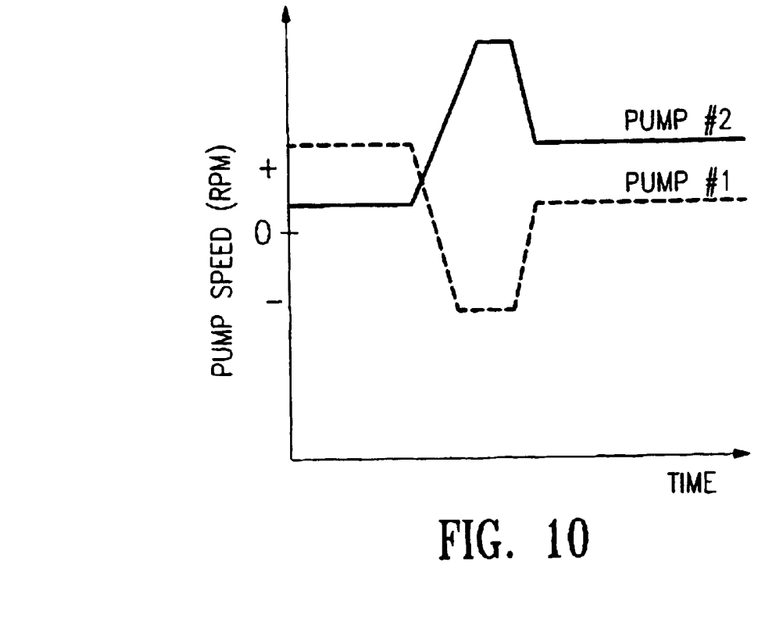
FIG. 10 is a graph of gear pump speed versus time useful in extruding polymeric tubes according to a method which embodies features of the invention, in which the second gear pump extruding the second layer being tapered from thin to thick is temporarily sped up beyond the steady state operating speed of the pump used to form a section of the shaft after the cotapered section.

In the embodiment illustrated in FIG. 9, the speed of the second gear pump 64 is increased to a speed setting of about 2 rpm to about 60 rpm, in, about 0.1 seconds to about 2 seconds, to form the outer layer in the cotapered section 71, and the outer layer 27 of the distal shaft section 73 is formed once the second gear pump reaches that increased steady state speed setting. In an alternative embodiment shown in FIG. 10, illustrating a graph of the gear pump speed versus time, the speed of the second gear pump is temporarily set to a greater speed of about 10 to about 100 rpm for about 0.25 seconds to about 1 second to form the outer layer of the cotapered section 71, and thereafter decreased to the steady state speed of about 2 rpm to about 60 rpm, preferably about 5 rpm to about 7 rpm, to form the outer layer of the distal shaft section 73. The proximal shaft section inner layer 26 has a thickness of about 0.0025 inch to about 0.004 inch, and the proximal shaft section outer layer 27 has a thickness of about 0.0005 inch or about 0.001 inch to about 0.002 inch. The distal shaft section inner layer 26 has a thickness of about 0.0025 inch to about 0.004 inch, and the distal shaft section outer layer 27 has a thickness of about 0.0005 inch or about 0.001 inch to about 0.002 inch. The length of the cotapered section 71 is about 5 inch to about 30 inch (13 cm to about 76 cm), and more specifically about 10 inch to about 15 inch (25 cm to about 38 cm), and preferably about 5 inch to about 10 inch. The length of the distal shaft section is typically about 12 inch to about 15 inch, and the length of the proximal shaft section is typically about 40 inch to about 45 inch. Upon exiting from the extrusion die 66, the extrudate 70 is typically quenched in a water bath, and may be further processed by conventional extrusion processing methods.

In one embodiment, the viscosity of the polymers used to form the first and second layers 26/27 is selected to minimize back pressure between the gear pumps 64 and the die 66. More specifically, the polymer forming the inner layer and the polymer forming the outer layer each have a relatively high melt flow index. Consequently, in one embodiment, shorter cotapered sections 71 are formed due to the decreased time required to release molten polymer compressed energy following changes in the gear pump settings during extrusion of the cotapered section. In a presently preferred embodiment, the inner layer polymer has a melt flow index of about 10 to about 20 grams/10 minutes, and preferably about 12 grams/10 minutes, and the outer layer polymer has a melt flow index of about 10 to about 20 grams/10 minutes, and preferably about 12 grams/10 minutes. The melt flow index of the polymer forming the inner layer may equal to or different from the melt flow index of the polymer forming the outer layer. As a consequence of the relatively high melt flow index of about 10 to about 20 grams/10 minutes, the polymer has a relatively low melt viscosity. The melt flow index is an inherent property of the polymer material which depends upon characteristics such as the molecular weight of the material. Exemplary polymeric materials having a melt flow index of about 10 to about 20 grams/10 minutes include polyolefins.

Figure 12:
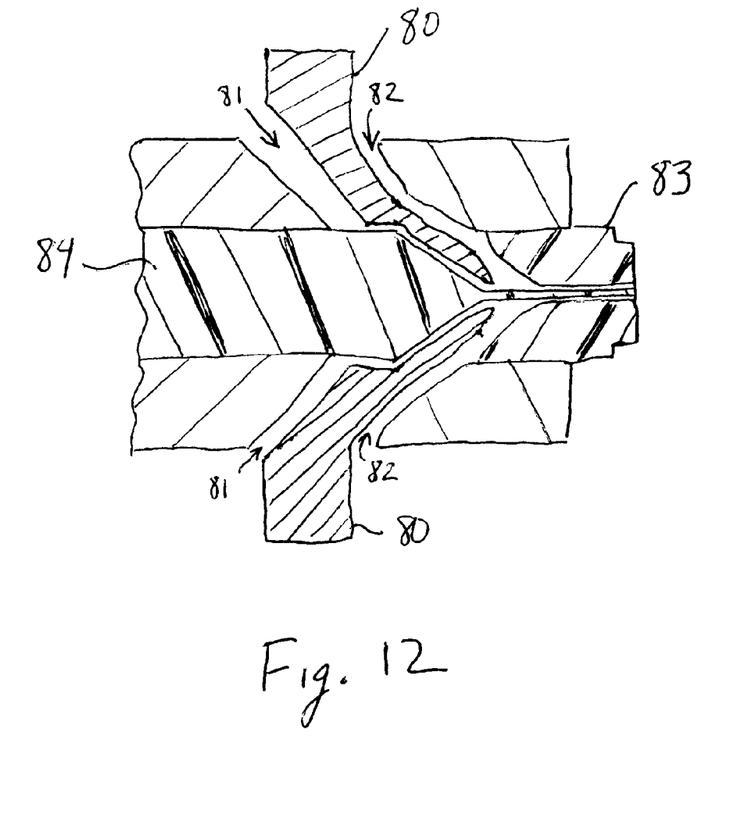
FIG. 12 is an schematic block diagram of a co-extrusion apparatus having an extended flow divider useful in extruding polymeric tubes according to a method which embodies features of the invention.

In one embodiment, the extrusion apparatus is provided with an extended flow divider. FIG. 12 illustrates extended flow divider 80, which separates the flow of the first polymer 81 from the second polymer 82 upstream of the die 83, and which extends closer toward the die exit than does a standard flow divider. In the illustrated embodiment, the extended flow divider 80 extends to the end of the tapered section of the tip 84, in contrast to a standard flow divider which extends only to the interface between the uniform diameter section of the tip 84 and the tapered section of the tip 84. Thus, the extended flow divider 80 reduces the amount of the second polymer 82 present where the two polymers 81/82 meet upstream of the die 83, such that the first polymer 81 displaces the second polymer 82 faster than with a standard flow divider, to thereby provide shorter cotapered transition lengths. The extended flow divider reduced the transition length by about 50% and specifically to about 10 inches to about 15 inches, increased the total layer thickness change by about 15%, and increased the transition rate by about 80% in a cotapered transition, compared with a cotapered transition formed using a standard flow divider.

The dimensions of catheter 10 are determined largely by the size of the guidewires to be employed and the size of the artery or other body lumen through which the catheter must pass or the size of the stent being delivered. Typically, the outer tubular member 16 has an outer diameter of about 0.02 to about 0.04 inch (0.05 to 0.10 cm), usually about 0.037 inch (0.094 cm), an inner diameter of about 0.015 to about 0.035 inch (0.038 to 0.089 cm), usually about 0.03 inch (0.076 cm). The wall thickness of the outer tubular member 16 can vary from about 0.002 to about 0.008 inch (0.0051 to 0.0201 cm), typically about 0.003 inch (0.0076 cm). The inner tubular member 18 typically has an outer diameter of about 0.019 to about 0.028 inch, usually about 0.021 inch. The overall working length of the catheter 10 may range from about 100 to about 150 cm, and is typically about 147 cm. Preferably, balloon 15 may have a length about 0.5 cm to about 4 cm and typically about 2 cm with an inflated working diameter of about 1 to about 8 mm, and for coronary applications about 1.5 mm to about 5 mm.

To the extent not discussed herein, the various catheter components can be formed of conventional materials. Inner tubular member 18 and outer tubular member 16 can be formed from materials already found useful in intravascular catheters such a polyethylene, polyvinyl chloride, polyesters, polyamides, polyimides and composite materials. The various components may be joined by heat bonding or use of adhesives.

The catheter shaft having at least first and second cotapered layers in accordance with the invention may be provided with additional layers on an inner or an outer surface of the shaft, such as a lubricious inner liner, one or more outer stiffening layers, reinforcement layers, and the like, coextruded with the first and second layers or separately applied thereto.

A variety of suitable catheter designs may be used, including rapid exchange, over-the-wire, and fixed wire catheter designs. A rapid exchange catheter generally includes an inflation lumen extending from the proximal end of the catheter shaft to a location spaced proximal to the distal end of the catheter shaft, a distal guidewire port in the distal end of the catheter shaft, a proximal guidewire port spaced distal to the proximal end of the catheter shaft, and a guidewire lumen extending between the proximal and distal guidewire ports. Typically, the proximal guidewire port is spaced a substantial distance from the proximal end of the catheter shaft and a relatively short distance from the distal guidewire port, so that the proximal guidewire port is closer to the distal guidewire port than to the proximal end of the catheter shaft.

Although not illustrated, the balloon catheter of the invention may be used to deliver prostheses, such as expandable stents, grafts, and the like, to a desired location within the patient's vasculature. A stent (not shown) comprising an expandable tubular body, typically having an open-walled structure, may be mounted on balloon 15, and balloon 15 may be inflated to expand the stent and seat it in the vessel. Additionally, catheter 10 may be used to touch up a previously implanted stent by positioning balloon within stent lumen and expanding the balloon to further expand the stent within a body lumen.

While the present invention is described herein in terms of certain preferred embodiments, those skilled in the art Will recognize that various modifications and improvements may be made to the invention without departing from the scope thereof. For example, although intermediate shaft sections 38/40 are illustrated between the first longitudinal section 32 and the second longitudinal section 34 in some embodiments but not in others, it should be understood that such intermediate sections may be provided or omitted on any of the embodiments. Although the tapered sections are illustrated as straight, linear tapers, the tapers may have a variety of suitable shapes including hyperbolic, curved shapes, by controlling extrusion conditions such as the speed of the gear pumps over time over the length of the profile. Additionally, although discussed primarily in terms of a catheter shaft, it should be understood that the invention can be used for a variety of polymeric tubular members used as catheter components such as sheaths, balloon tubes, and the like. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An intraluminal catheter, comprising an elongated shaft having a proximal end, a distal end, at least one lumen, a first layer, a second layer, the first layer being an inner layer relative to the second layer, and having
    a) a first longitudinal section with the first layer having a tapered surface, and the second layer having an inversely tapered surface; and
    b) a second longitudinal section with a tapered outer diameter, and the first layer having a tapered inner surface and a tapered outer surface in the second longitudinal section of the catheter shaft, and the second layer having a substantially constant wall thickness in the second longitudinal section of the catheter shaft.

2. The catheter of claim 1 wherein the first longitudinal section of the catheter shaft is proximal to the second longitudinal section of the catheter shaft.

3. The catheter of claim 2 wherein the catheter shaft includes a third longitudinal section distal to the second longitudinal section of the catheter shaft, with a substantially constant outer diameter less than the outer diameter of the first longitudinal section of the catheter shaft, the first layer having a tapered surface, and the second layer having an inversely tapered surface.

4. The catheter of claim 1 wherein the first and second layers are continuous layers extending from the proximal end to the distal end of the catheter shaft.

5. The catheter of claim 1 wherein the proximal end of the second layer is distal to the proximal end of the first layer, and the distal end of the first layer is proximal to the distal end of the second layer.

6. The catheter of claim 1 wherein the catheter is a balloon catheter having a balloon secured to at least a section of the catheter shaft with an interior in fluid communication with the shaft lumen.

7. The catheter of claim 6 wherein the shaft comprises an outer tubular member defining an inflation lumen in fluid communication with the balloon, and the shaft includes an inner tubular member disposed within the inflation lumen defining a guidewire lumen, and wherein the balloon has a proximal end sealingly secured to a distal section of the outer tubular member and a distal end sealingly secured to a distal section of the inner tubular member.

8. The catheter of claim 1 wherein the first longitudinal section of the shaft has a length of about 13 cm to about 76 cm.

9. An intraluminal catheter, comprising an elongated shaft having a proximal end, a distal end, at least one lumen, a first layer having an inner surface tapering distally to a smaller inner diameter, a second layer, and having
   a) a first longitudinal section with the first layer having a tapered surface, and the second layer having an inversely tapered surface; and
   b) a second longitudinal section distal to and directly adjacent to the first longitudinal section of the catheter shaft, with a tapered outer diameter, and the first layer having an outer surface tapering distally to a smaller outer diameter in the second longitudinal section of the catheter shaft and the second layer having an outer surface tapering distally to a smaller outer diameter in the second longitudinal section of the catheter shaft.

10. The catheter of claim 9 wherein the first longitudinal section has a substantially constant outer diameter.

11. An intraluminal catheter, comprising an elongated shaft having a proximal end, a distal end, at least one lumen, and having at least a section having cotapered first and second layers, so that the first layer has a tapered surface and the second layer has an inversely tapered surface, the first layer being formed of a polymer having a melt flow index of about 10 to about 20 grams/minute, and the second layer being formed of a polymer having a melt flow index of about 10 to about 20 grams/minute.

12. The catheter of claim 11 wherein the melt flow index of the first layer polymer is not greater than the melt flow index of the second layer polymer, and the first layer polymer has a higher Shore durometer hardness than the second layer polymer.

13. An intraluminal catheter, comprising an elongated shaft having a proximal end, a distal end, at least one lumen, a first layer, a second layer, the first layer being an inner layer relative to the second layer, and having
   a) a first longitudinal section with the first layer having a tapered surface, and the second layer having an inversely tapered surface;
   b) a second longitudinal section with a tapered outer diameter, and the first layer has a substantially constant wall thickness in the second longitudinal section of the catheter shaft, and the second layer has a tapered inner surface and a tapered outer surface in the second longitudinal section of the catheter shaft; and
   c) a shaft section between and directly adjacent to the first and second longitudinal sections of the catheter shaft, having a constant outer diameter and a constant interfacial diameter between the first and second layers.

14. An intraluminal catheter, comprising an elongated shaft having a proximal end, a distal end, at least one lumen, a first layer having a proximal and a distal end, a second layer having a proximal end located distal to the proximal end of the first layer and a distal end located distal to the distal end of the first layer, and having
   a) a first longitudinal section with the first layer having a tapered surface, and the second layer having an inversely tapered surface; and
   b) a second longitudinal section with a tapered outer diameter, at least one of the first or second layers having a tapered inner surface and a tapered outer surface in the second longitudinal section of the catheter shaft, and at least one of the first or second layers having a substantially constant wall thickness in the second longitudinal section of the catheter shaft.

15. An intraluminal catheter, comprising an elongated shaft having a proximal end, a distal end, at least one lumen, a first layer, a second layer, the first layer being an inner layer relative to the outer layer, and having
   a) a first longitudinal section with the first layer having a tapered surface, and the second layer having an inversely tapered surface;
   b) a second longitudinal section with a tapered outer diameter, at least one of the first or second layers having a tapered inner surface and a tapered outer surface in the second longitudinal section of the catheter shaft, and at least one of the first or second layers having a substantially constant wall thickness in the second longitudinal section of the catheter shaft; and
   c) an inner liner having a substantially constant wall thickness on an inner surface of the first layer.

* * * * *